United States Patent [19]

Malfitano

[11] 4,433,972
[45] Feb. 28, 1984

[54] SANITARY NAPKIN

[76] Inventor: Amanda Malfitano, 161-77th St., Brooklyn, N.Y. 11209

[21] Appl. No.: 269,392

[22] Filed: Jun. 1, 1981

[51] Int. Cl.³ .................................. A61F 13/16
[52] U.S. Cl. ....................................... 604/385
[58] Field of Search .......... 128/290 R, 290 P, 290 W, 128/287; 604/358–360, 365–366, 385

[56] References Cited

U.S. PATENT DOCUMENTS

| | | | |
|---|---|---|---|
| 1,914,596 | 6/1933 | Diehl | 604/358 |
| 2,331,355 | 10/1943 | Strongson | 604/365 |
| 2,731,014 | 1/1956 | Hollinsworth | 604/365 |
| 2,964,040 | 12/1960 | Ashton et al. | 604/366 |
| 3,172,817 | 3/1965 | Leupold et al. | 424/28 |
| 3,183,909 | 5/1965 | Roehr | 604/385 |
| 3,431,911 | 3/1969 | Meisel, Jr. | 604/360 |
| 3,532,097 | 10/1970 | Jones, Sr. | 604/366 |

*Primary Examiner*—C. Fred Rosenbaum
*Assistant Examiner*—Sherri Vinyard

[57] ABSTRACT

A sanitary napkin comprising a backing sheet and a face sheet having an absorbent pad assembly sandwiched therebetween. The pad assembly includes two pads, there being a relatively large pad of wood fluff or like absorbent material, and a substantially diamond shape second pad of lesser dimensions seated on said first pad for transmitting fluid thereto. The second pad is impregnated with a germicide.

5 Claims, 4 Drawing Figures

SANITARY NAPKIN

BACKGROUND OF THE INVENTION

1. Field of the Invention

This invention relates to a personal care product and more particularly to a sanitary napkin.

2. Description of the Prior Art

In the past sanitary napkins have been devised for placement and support at the crotch portions of the user. Alternatively tampons have been used by many women who favor the feeling of security that the intimate contact of the tampon provides. However tampons have proved dangerous to the health of the user and often can cause irritation.

In connection with both prior art tampons and even sanitary napkins certain dangers to the health of the user can occur due to bacterial growth and retention of fluids too close to the users vaginal orifice.

SUMMARY OF THE INVENTION

The present invention overcomes the disadvantages of the prior sanitary napkins and tampons by providing for the feeling of intimate contact and for the feeling of security by removing menstrual fluids from the immediate area of the vaginal orifice and by providing for better absorption of fluids that have at least been partially chemically sterilized.

In accordance with the invention the sanitary napkin comprises a backing sheet having two super posed absorbent pads thereon. The inner most pad is substantially diamond shape and is impregnated with a germicide or bacteriacide. This pad is made of open cell foamed material for rapid conveyance of menstrual fluids to the others pad 14 for absorbing such fluid.

DETAIL DESCRIPTION OF THE INVENTION

Figure 1:
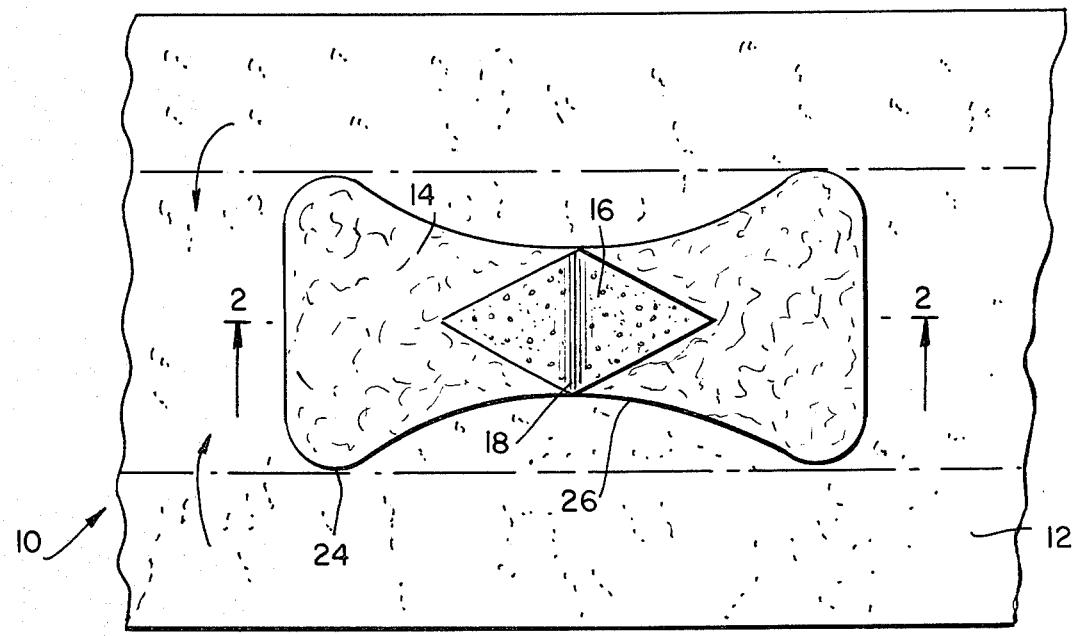
FIG. 1 is a plan view of a sanitary napkin according to the invention.
Figure 2:
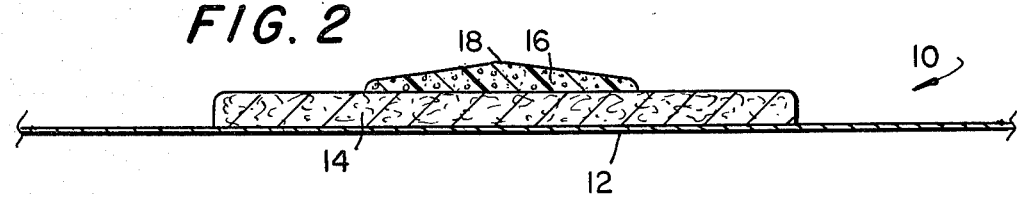
FIG. 2 is a horizontal section of view taken along the plane of Line 2—2 in FIG. 1 with the gauze wrapping removed therefrom.
Figure 3:
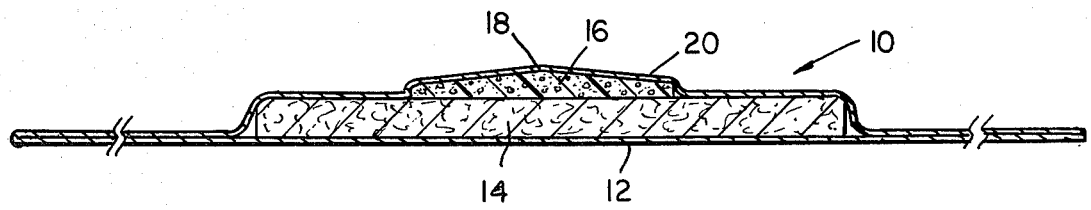
FIG. 3 is a view similar to FIG. 2 shown as a completed napkin.
Figure 4:
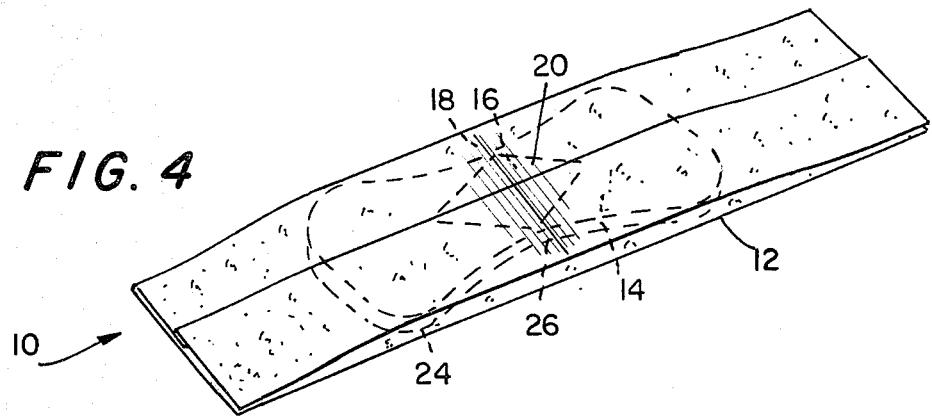
FIG. 4 is a perspective view of the sanitary napkin.

The sanitary napkin 10 according to the invention employs a backing sheet 12 preferably of fluid impervious material such as polyethlethlene. Disposed on the backing sheet 12 is a first absorbent pad 14 formed of gauze wrapped wood fluff, cotton or like absorbent material. Disposed on the pad 14 is a second pad 16 formed of open cell foamed polyurethane. This pad 16 is of a generally diamond or oval shape and is thicker in the center thereof to form an apex 18. The pad 16 is also wider at is center in accordance with is diamond shape. The pad 16 is impregnated with a germicide or bacteriacide known in the art.

Wrapped about the entire napkin is a gauze wrapper 20 in one or more thickness which may underly the backing sheet 12, the ends serving for attanment to a conventional sanitary napkin belt. The wrapper 20 also serves as a face sheet.

In use, the protruding diamond shaped pad 16 intimately engages the vaginal area of the user, even so far as partial penetration thereby affording intimate contact and a feeling of security which may be desired while minimizing leakage and serving to accommodate gushes of menstrual fluids while conveying such fluids to the absorbent pad 14 for rentention. The pad 16 provides better accomodation of gushes of fluid then the material of the absorbent pad 14 and prevents build up of bacteria which might cause adverse reaction to the users health.

In order to assist in directing the diamond shaped pad 16 to partially penetrate the vaginal area, the absorbent pad is hourglass shaped or inwardly contoured as at 26.

I claim:

1. A sanitary napkin comprising an absorbent pad assembly, including a first absorbent pad for underlying the crotch area of the user, and a second absorbent pad of lesser fluid retention ability and of a size to permit partial penetration of a vaginal orifice disposed on said first pad for immediate contact with the genital area of the user, said second pad conforming generally to the contour of the genital area of the user, said second pad being thicker and wider at its center forming an apex, said first pad being hourglass shaped to assist the penetration of the vaginal orifice by said second pad, and having a width at its narrowest point at the crotch area substantially the same as the width of the widest portion of said second pad.

2. A sanitary napkin according to claim 1, wherein said second pad is impregnated with a germicide.

3. A sanitary napkin according to claim 1, wherein said second pad is of a substantially diamond shape.

4. A sanitary napkin according to claim 3, wherein said second pad is impregnated with a substance for preventing bacterial growth.

5. A sanitary napkin according to claim 4, wherein said sanitary pad assembly includes a backing sheet of a waterproof material.

* * * * *